United States Patent
Tsouri et al.

(10) Patent No.: US 10,292,594 B2
(45) Date of Patent: May 21, 2019

(54) METHOD AND SYSTEM FOR CONTACTLESS DETECTION OF CARDIAC ACTIVITY

(71) Applicants: Gill R. Tsouri, Rochester, NY (US); Sohail Dianat, Pittsford, NY (US)

(72) Inventors: Gill R. Tsouri, Rochester, NY (US); Sohail Dianat, Pittsford, NY (US)

(73) Assignee: ROCHESTER INSTITUTE OF TECHNOLOGY, Rochester, NY (US)

( * ) Notice: Subject to any disclaimer, the term of this patent is extended or adjusted under 35 U.S.C. 154(b) by 103 days.

(21) Appl. No.: 14/215,686

(22) Filed: Mar. 17, 2014

(65) Prior Publication Data

US 2014/0276118 A1 Sep. 18, 2014

Related U.S. Application Data

(60) Provisional application No. 61/793,477, filed on Mar. 15, 2013.

(51) Int. Cl.
*A61B 5/00* (2006.01)
*A61B 5/024* (2006.01)

(52) U.S. Cl.
CPC ........ *A61B 5/0077* (2013.01); *A61B 5/02416* (2013.01); *A61B 5/7225* (2013.01)

(58) Field of Classification Search
None
See application file for complete search history.

(56) References Cited

U.S. PATENT DOCUMENTS

| 6,442,420 B1* | 8/2002 | Julu | A61B 5/0472 600/509 |
| 6,718,197 B1* | 4/2004 | Carlson | A61B 5/0468 600/515 |
| 2004/0167409 A1 | 8/2004 | Lo et al. | |
| 2005/0197552 A1 | 9/2005 | Baker, Jr. | |
| 2008/0161706 A1 | 7/2008 | Cho et al. | |
| 2008/0262326 A1 | 10/2008 | Hete et al. | |
| 2009/0033381 A1* | 2/2009 | Lee | H03L 7/085 327/156 |
| 2011/0137181 A1 | 6/2011 | Lin et al. | |
| 2011/0152701 A1 | 6/2011 | Buxi et al. | |
| 2011/0245697 A1 | 10/2011 | Miettinen | |
| 2012/0022348 A1* | 1/2012 | Droitcour | A61B 5/0507 600/323 |
| 2012/0136226 A1* | 5/2012 | Wilke | A61B 5/02405 600/324 |
| 2013/0079649 A1 | 3/2013 | Mestha et al. | |
| 2015/0141774 A1* | 5/2015 | Ogawa | A61C 17/22 600/301 |

OTHER PUBLICATIONS

Poh et al., "Non-contact, automated cardiac pulse measurements using video imaging and blind source separation," May 7, 2010, Optics Express, vol. 18, No. 10, pp. 10762-10774.*

(Continued)

*Primary Examiner* — Joseph M Santos Rodriguez
(74) *Attorney, Agent, or Firm* — Nond, Schoeneck & King, PLLC; Joseph Noto (57) ABSTRACT

A system and method include contactless detecting and tracking cardiac activity by making use of a feedback control system, such as a Phase Locked Loop (PLL), in real-time or from a prerecorded signal stream.

15 Claims, 6 Drawing Sheets

(56) References Cited

OTHER PUBLICATIONS

Sands et al., "Power Spectrum Analysis of Heart Rate Variability in Human Cardiac Transplant Recipients," 1989, American Heart Association, vol. 79, pp. 76-82.*
Phase-Locked Loop (PLL), Nov. 28, 2001, TechTarget, https://web.archive.org/web/20120202072634/http://searchnetworking.techtarget.com/definition/phase-locked-loop?vgnextfmt=print.*
Poh et al., "A medical mirror for non-contact health monitoring," Aug. 7, 2011, Proceeding SIGGRAPH '11 ACM SIGGRAPH 2011 Emerging Technologies Article No. 2.*
Chihiro Takano and Yuji Ohta, "Heart Rate Measurement Based on a Time-Lapsed Image," Medical Engineering & Physics 29 (2007) pp. 853-857.
Wim Verkruysse, Lars O. Svaasand, and J. Stuart Nelson, "Remote Plethysmographic Imaging Using Ambient Light," Optics Express, vol. 16, No. 26, Dec. 22, 2008, pp. 21434-21445.
Ming-Zher Poh, Daniel J. McDuff, and Rosalind W. Picard, "Non-Contact, Automated Cardiac Pulse Measurements Using Video Imaging and Blind Source Separation," Optics Express, vol. 18, No. 10, May 10, 2010, pp. 10762-10774.
Ming-Zher Poh, Daniel J. McDuff, and Rosalind W. Picard, "Advancements in Noncontact, Multiparameter Physiological Measurements Using a Webcam," IEEE Transactions on Biomedical Engineering, vol. 58, No. 1, Jan. 2011, pp. 7-11.
Gill R. Tsouri, Survi Kyal, Sohail Dianat, and Lalit K. Mestha, "Constrained Independent Component Analysis Approach to Nonobtrusive Pulse Rate Measurements," Journal of Biomedical Optics, 17(7), 077011 (Jul. 2012), pp. 1-4.
Marvin L. Appel and Richard J. Cohen, "Use of a Phase-locked Loop to Correct Heart Rate Variability Artifacts in Data From Human Cardiac Transplant Recipients," Computers in Cardiology Proceedings (1998), pp. 307-210.

* cited by examiner

METHOD AND SYSTEM FOR CONTACTLESS DETECTION OF CARDIAC ACTIVITY

CROSS REFERENCE

This application claims the benefit of the filing date of U.S. Provisional Patent Application Ser. No. 61/793,477, filed Mar. 15, 2013, which is hereby incorporated by reference in its entirety.

FIELD

The present invention relates to the field of contactless detecting of cardiac activity, and in particular contactless detecting of cardiac activity by making use of a feedback control system, such as a Phase Locked Loop (PLL).

BACKGROUND

Pulse rate is widely recognized as an important cardiovascular parameter for assessing a patient's health. Current methods of measuring pulse rate rely on the placement of electrodes on the patient's skin. Continuous monitoring using commercial pulse oximetry sensors attached to a finger or earlobe pose discomfort is susceptible to infections and could lead to irritation of the skin. In addition, these sensors must be placed and read by a qualified medical professional resulting in potential bottlenecks when attending to patients at healthcare facilities. Remote non-obtrusive monitoring is clearly an attractive alternative, provided that accurate measurements are obtained. Past attempts for remote non-obtrusive monitoring of the pulse rate include the use of PhotoPlethysmoGraphy (PPG). In PPG, a dedicated light source is used to capture the Blood Volume Pulse (BVP) by observing variations in reflected light due to pulsatile blood volume. Spectral estimation is then applied to the BVP to extract the pulse rate.

Recent work focused on obtaining the BVP using ambient light rather than a dedicated light source. This work pioneered an approach to extract pulse rate measurements and PPG signals using digital RGB cameras. The accuracy of such methods was improved on by applying blind source separation using Independent Component Analysis (ICA) and incorporating face tracking to automatically capture the face of a single or multiple patients. The work used a webcam to capture the video and was recently expanded to include measurements of other parameters such as the Heart Rate Variability (HRV) based on the ICA approach.

ICA is used to extract underlying statistical Independent Components (ICs) responsible for the observed signals. It assumes the observed signals are the result of a linear mixture of independent sources. The number of sources is equal to the number of observations, i.e., the linear mixture model is represented by a square matrix. Standard ICA techniques suffer from a sorting problem: the independent components are not ordered, meaning that the source signal of interest could be present in any of the ICA outputs. Previous work recognized the sorting problem and resolved it either by always selecting the second IC or by selecting the component for which the peak frequency has the highest power. In a recent contribution, constrained ICA (cICA) was used to improve the accuracy of BVP measurements using a webcam by solving the sorting problem of ICA.

Known methods rely on block processing, where a signal must be recorded for from 15 to 60 seconds and the only cardiac information obtained from the signal is the average heart rate during the recording. State-of-the-art methods depending on the use of ICA and cICA algorithms are computationally intensive and complex. This means that implementation must rely on a bulky and powerful computer and that latency in obtaining a result is inevitable. In addition, power consumption and heat dissipation are a concern when designing compact devices.

SUMMARY OF THE INVENTION

In accordance with one aspect of the present invention, there is provided a method for contactless detection of cardiac activity of a subject, including capturing a signal from incident light reflected off the skin of the subject; and feeding the captured signal to a feedback control system designed to lock and track a frequency corresponding to an expected range of heart rate; and tracking the frequency over time.

In accordance with another aspect of the present invention, there is provided a system for contactless detection of cardiac activity of a subject, including a detector designed to capture a signal from incident light reflected off the skin of the subject; a feedback control system in signal communication with the detector, the feedback control system designed to lock and track a frequency of the signal frequency produced by the detector corresponding to an expected range of heart rate; and optionally, a device designed to exhibit the frequency of the tracked signal over time.

In accordance with another aspect of the present invention, there is provided a method for contactless detection of cardiac activity of a subject operating a motor vehicle, including providing in the motor vehicle a system including a detector configured to produce a signal from incident light from the skin of the subject operating the motor vehicle hitting the detector; a feedback control system in signal communication with the detector, the feedback control system designed to lock and track a frequency of the signal produced by the detector corresponding to an expected range of heart rate; producing a signal from incident light from the skin of the subject hitting the detector; feeding the signal to the feedback control system; and tracking the frequency over time.

In accordance with another aspect of the present invention, there is provided a method for contactless detection of cardiac activity of a subject passing a security checkpoint, including providing at the security checkpoint a system including a detector configured to produce a signal from incident light from the skin of the subject passing a security checkpoint hitting the detector; a feedback control system in signal communication with the detector, the feedback control system designed to lock and track a frequency of the signal produced by the detector corresponding to an expected range of heart rate; producing a signal from incident light from the skin of the subject hitting the detector; feeding the signal to the feedback control system; and tracking the frequency over time.

In accordance with another aspect of the present invention, there is provided a method for contactless detection of cardiac activity of a subject in a psychological evaluation, including providing in the psychological evaluation a system including a detector configured to produce a signal from incident light from the skin of the subject to be evaluated hitting the detector; a feedback control system in signal communication with the detector, the feedback control system designed to lock and track a frequency of the signal produced by the detector corresponding to an expected range of heart rate; producing a signal from incident light from the skin of the subject hitting the detector; feeding the signal to the feedback control system; and tracking the frequency over time.

In accordance with another aspect of the present invention, there is provided the above methods, wherein the tracked heart rate frequency is analyzed to determine a physiological condition of the subject.

These and other aspects of the present invention will become apparent upon a review of the following detailed description and the claims appended thereto.

DETAILED DESCRIPTION

Figure 1:
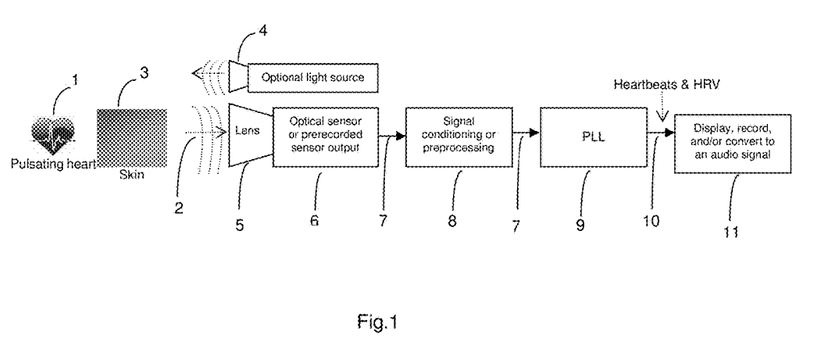
FIG. 1 is a block diagram illustrating a system and method for detecting and tracking cardiac activity in accordance with an embodiment of the present invention.

The present invention includes an apparatus for and a method of detecting and tracking cardiac activity by using a feedback control system, such as a Phase Locked Loop (PLL), designed to lock and track over time a frequency corresponding to an expected range of heart rate. FIG. 1 shows a functional block scheme of an embodiment for a method incorporating a PLL in accordance with the present invention. The invention may include other types and numbers of electronic feedback control systems, devices, and components which are configured in other manners. The usefulness of the invention comes from the ability to provide immediate real-time beat by beat detection using low computation power and low power consumption.

In accordance with an embodiment as shown in FIG. 1, contactless detection of cardiac activity of a pulsating heart 1 of a subject includes capturing a signal from incident light 2 reflected off the skin 3 of the subject. The incident light 2 can originate from ambient light or light from a dedicated light source 4 or both. The incident light 2 illuminates the skin 3 of the subject, which illumination can be used to monitor cardiac activity. Since the pulsating heart 1 pumps blood to the skin 3 in a periodic pattern, the intensity of reflected light off the skin 3 has the same periodic behavior as the pulsating heart 1. The reflected light can be captured as a signal, such as being gathered by a lens 5, or other device known in the art, and input to a sensor 6, such as an optical sensor, or other sensor known in the art, which generates an electrical signal 7 at the output of the sensor. In this manner, a real-time signal can be generated from the reflected light over time. Alternatively, the reflected light can be recorded for off-line feeding of the captured signal to a feedback control system designed to lock and track over time a frequency corresponding to an expected range of heart rate. In this manner, a prerecorded signal stream can take the place of the real-time sensor output. An RGB webcam is one example of such a sensor and the potential source for a recorded stream. An Infra Red (IR) sensor is another example of such a sensor. Other devices for obtaining a recorded signal stream are known in the art. The real-time or recorded signal may preferably undergo signal conditioning and/or processing 8 prior to the signal 7 being fed to a feedback control system 9 by manners known in the art, e.g., filtering for limiting the frequency range, Automatic Gain Control (AGC), noise reduction, and the like. In a preferred embodiment, the processed signal is fed as an input signal to a feedback control system, such as a PLL. The above description illustrates embodiments for capturing a signal from incident light reflected off the skin in real-time or recording for off-line use.

The feedback control system in accordance with the present invention is a system designed for extracting an underlying frequency from an input signal. In general, in an embodiment the feedback control system does this by comparing the input signal with an internal signal by evaluating a selected function over the two signals. The outcome of the function is processed to provide an error signal representing the lack of synchronization between the signals. This error signal is used to change the internal signal in an effort to synchronize the signals. Preferably, the error signal converges to zero over time and the corresponding internal signal exhibits the same underlying frequency of the input signal. A suitable example of a feedback control system in accordance with the present invention is a PLL, which refers to circuits/algorithms that in accordance with known methods can be made to lock fast to an unknown underlying frequency and track the change in the locked frequency over time. For example, communication and control systems make extensive use of PLL's for synchronization, frequency synthesis, and for stabilizing dynamic systems. The feedback control system can be constructed in other manners using other components.

In an embodiment of the present method, one PLL is used to lock on to the periodic pattern of the beating heart and track the heart's behavior as is reflected in the electrical signal at the PLL input to detect any changes. By doing so, the output 10 of this PLL provides a minor of cardiac activity including the occurrences of heartbeats, Heart Rate Variability (HRV), and heart rate disorder. The output 10 including the tracked heart rate variability can be optionally displayed, recorded, and/or converted to an audio signal by an appropriate device 11.

Figure 2:
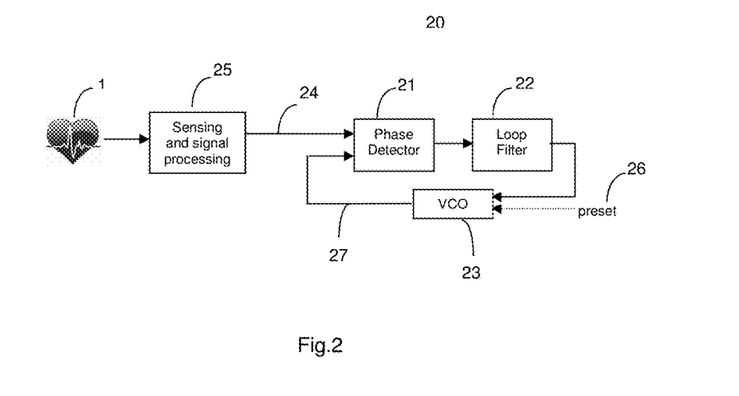
FIG. 2 is a block diagram illustrating a system for detecting and tracking cardiac activity in accordance with an embodiment of the present invention.

FIG. 2 shows an embodiment of a functional block scheme for a PLL 20 in accordance with the present invention. In an embodiment as shown in FIG. 2, a PLL 20 constructed of a phase detector 21 connected between a loop filter 22 and a Voltage Controlled Oscillator (VCO) 23 is used in a feedback loop to lock on and track an underlying frequency in the input signal 24 which undergoes sensing and processing 25. In this example, a preset 26 voltage is fed to the VCO 23 to set the VCO 23 output frequency to 1.2 Hz corresponding to a heart rate of 72 Beats Per Minute (BPM). Once the PLL locks on to the incoming signal frequency, the feedback loop ensures that the phase detector output is zero at any given time (indicating that tracking is achieved). This can be achieved by designing the loop filter in accordance with the dynamic nature of the input signal. More specifically, the order of the loop filter is selected to be the same order of the input signal as presented in the Laplace domain and the bandwidth of the loop filter is set to filter as much noise as possible, while maintain stability of the feedback loop and fast convergence time. The PLL is designed to lock and track a changing heart rate in a continuous fashion.

FIG. 2 shows a PLL designed to track an input frequency heart rate that operates in a manner where the changing pulse rate (frequency) holds information about the heart activity (information signal). Under this embodiment, the VCO output mirrors the pulsating heart activity. Zero crossings at the VCO output indicate heartbeats. The varying signal at the input to the PLL mirrors cardiac activity, such as HRV. The loop filter is preferably designed according to expected variability in pulse, pulse range, and expected noise and interference superimposed over the sensed signal.

The present invention can be used to perform noncontact monitoring of a subject's beat by beat cardiac activity. Beat by beat cardiac activity is indicative to many ailments and physiological and mental states. Elevated pulse, arrhythmia and stress/relaxation levels through the relationship between HRV and vagal tone activity are some examples. Many applications can be developed based on this invention, which include the following examples. One application is the long term, continuous and automated monitoring of patients in healthcare facilities and residential environments (currently conventional monitoring is occasional and requires a qualified care provider). Another application is the ability to monitor patients in prolonged CAT scans (currently this is not possible with conventional monitors because no electrodes are allowed in the scanner). Another application is the monitoring of babies without electrodes (as their skin is easily irritated). This process can be used to flag suspicious individuals in places with heightened security sensitivity, such as airports. The present invention can be used as an assistive tool for interrogations and questioning by law enforcement agencies. Further, drivers can be monitored in cars for over-relaxation and over-stressful states, both equally dangerous for passengers' safety.

The present invention offers substantial advantages over the prior technology in at least the areas of granularity and complexity. In contrast to the prior technology, the present invention allows for improved granularity by enabling beat by beat detection which offers much more information on cardiac activity and enables accurate detection of HRV and underlying heart conditions. The present invention can be implemented using readily available off-the-shelf miniature electrical components resulting in a compact design which consumes and dissipates much less power and suffers from no latency in measurement as compared to know techniques.

The invention can be implemented using software on a PC/smartphone/tablet for processing signals output from an RGB camera in real-time or from a prerecorded video stream. Face tracking known in the art can be used to identify and track a subject's face as the portion of skin to be observed.

The invention can be implemented in hardware using analog and/or digital electronics to form a very compact device that is capable of replacing the known finger-probe oximeter. The device of the present invention can be placed on a subject's collar where light reflected off the skin of the neck is used to continuously track cardiac activity.

A similar device can be integrated into eyeglasses, allowing the wearer to evaluate the cardiac activity of a person they are interacting with. The PLL output signal can be easily converted to an audio signal, allowing the wearer to hear the other person's pulse in real-time. The applications of such glasses range from diagnosis of patients in a health care setting to use in law enforcement.

The invention will be further illustrated with reference to the following specific examples. It is understood that these examples are given by way of illustration and are not meant to limit the disclosure or the claims to follow.

EXAMPLES

The present invention was implemented in software using the PLL design depicted in FIG. 2. Multiple video streams of the faces of over 40 subjects were recorded while measuring each subject's heart rate using a prior art finger-probe oximeter. The video streams were used to measure heartbeats with both (a) the comparative cICA algorithm disclosed in Tsouri et al. "Constrained-ICA Approach to Non-Obtrusive Pulse Rate Measurements," *SPIE Journal of Biomedical Optics*, July 2012 and (b) the PLL-based system of the present invention. The outputs of each methods (a) and (b) were compared to the finger-probe oximeter output reading of the prior art. The results indicate that the method of the present invention was able to extract average heart rate and track varying heart rate. See FIGS. 3-6 for representative results.

Results recorded in the video stream for subject number 24 from the set of recordings are presented in this example. This 60 second RGB video was recorded using 15 frames per second. Face tracking software was used to identify the facial region of interest. RGB traces were generated from the identified facial region by taking the average red, green and blue pixel intensity per frame. The traces obtained are shown in FIG. 3.

Next, the prior art cICA algorithm noted above in method (a) was applied to the RGB traces to extract an average heart rate over the 60 second recording. The comparative data is set forth in FIG. 4. The result was a pulse of 52, compared to a pulse of 51 measured using the finger-probe oximeter.

Figure 3:
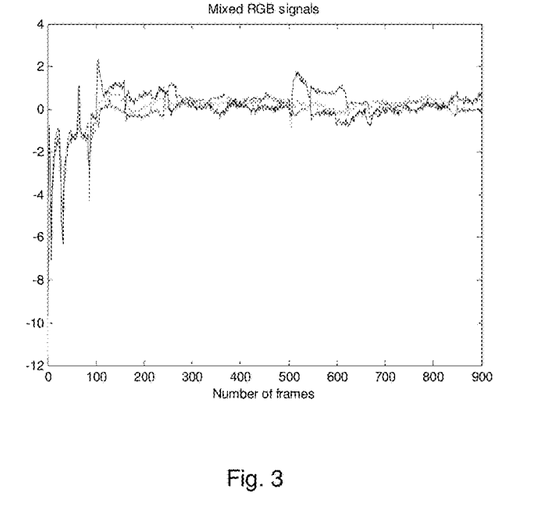
FIG. 3 is a graph of the average red, green, and blue pixel intensities per number of frames reflected from a facial region.
Figure 4:
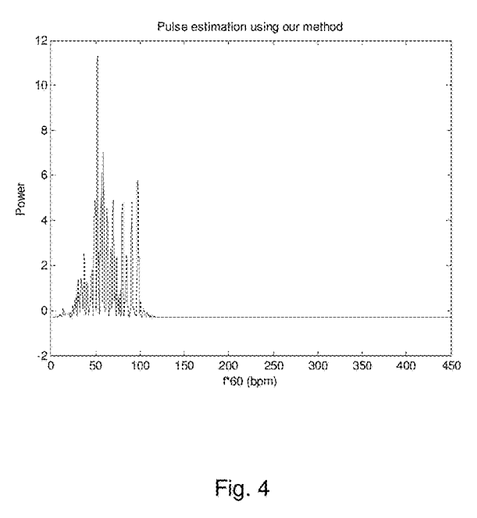
FIG. 4 is a graph of the power spectral density of an output signal in accordance with a comparative process.
Figure 5:
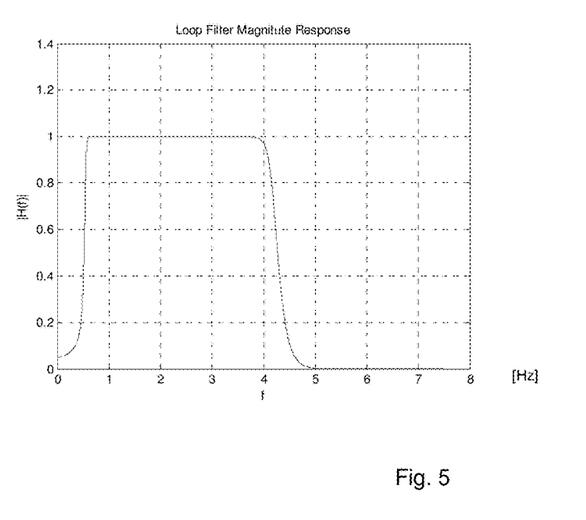
FIG. 5 is a graph of the magnitude response of the loop filter in accordance with an embodiment of the present invention.

In accordance with the invention, the green trace signal from the mixed RGB signals shown in FIG. 3 was band-pass filtered in the step 25 shown in FIG. 2 using a filter with the magnitude response corresponding to an expected heart rate of from 35 to 240 BPM. The resulting graph of the filtered signal 24 is shown in FIG. 5, wherein frequency is reported in hertz.

The green trace was chosen because it was established in the literature that the green color exhibits the strongest absorption in blood of all the three RGB traces. The filtered green trace, shown as the signal 24 of FIG. 2, was input to the phase detector 21 of the PLL in accordance with the present invention. The output signal 27 from the VCO 23 is fed to the phase detector 21. The results are shown in FIGS. 6A-6D.

Figure 6A:
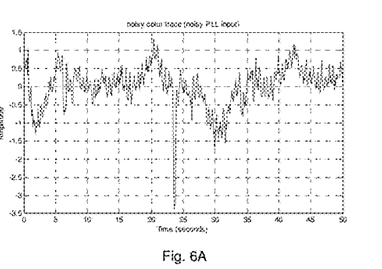
FIG. 6A is a graph of the color trace at the PLL input.
Figure 6B:
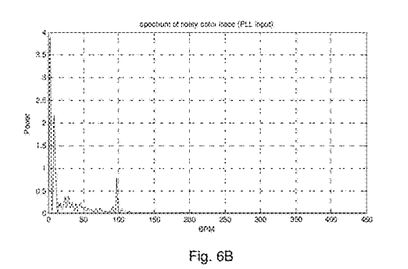
FIG. 6B is a graph of the spectrum of the color trace at the PLL input.
Figure 6C:
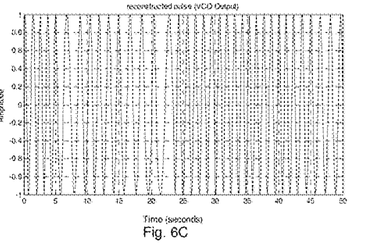
FIG. 6C; is a graph of the reconstructed pulse at the VCO output.

FIG. 6A illustrates the green trace signal used as the input signal 24 to the PLL and FIG. 6B presents spectral content of the input signal 24. It is evident from FIG. 6B that the input signal 24 is noisy and that the underlying heart-rate frequency is not clearly identifiable. However, when observing the VCO output signal 27 (the PLL internal signal) in FIG. 6C and FIG. 6D, the heart-rate underlying frequency is clearly visible in both time and spectrum. Thus, the PLL was successful in extracting a signal minoring cardiac activity from a noisy sensed signal.

Figure 6D:
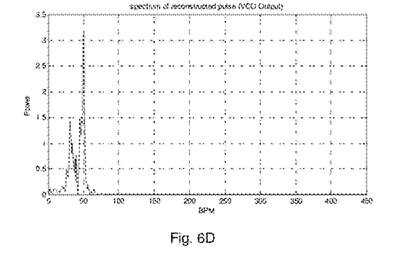
FIG. 6D is a graph of the spectrum of the reconstructed pulse at the VCO output.

The spectrum of the VCO output shown in FIG. 6D, indicates that the detected average pulse was 59.5, compared to an average pulse of 51 measured using the finger-probe oximeter. However, this apparent difference is due to an averaging performed over a varying pulse as detected by the present invention. A finer real-time granularity in the analysis of the heart rate is obtainable by the current invention, as compared to known methods. Looking at the VCO output in time as illustrated from the graph in FIG. 6C, it is apparent that the pulse varied during the recording—the heart rate is high during the first 5 seconds, it is then decreased during seconds 5-10, increasing again during seconds 10-20, and so on. This information about the varying pulse, which can be analyzed to determine a physiological condition of the subject, obtainable by the present invention is unobtainable in real-time by known methods using cICA and ICA-based algorithms. ICA and cICA algorithms rely on offline processing of a recorded signal typically 30 to 60 seconds long and so provide results with latency. In addition, using ICA or cICA algorithms would require the use of significant processing power, not needed in the current invention.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for contactless detection of cardiac activity of a subject, comprising:
   monitoring blood volume pulse in real-time comprising detecting a first pulse resulting from a first contraction of the heart prior to the following contraction of the heart on a pulse by pulse basis through the skin of the subject with a contactless sensor by capturing with the sensor incident light reflected off the skin representing the pulse of the subject;
   converting an optical signal of the reflected light to an electrical signal comprising a frequency;
   feeding the captured electrical signal to a feedback control system;
   locking and tracking over time the frequency of the captured electrical signal within a range corresponding to an expected range of heart rate using the feedback control system;
   measuring the frequency of the electrical signal at the output of the feedback control system;
   extracting the pulse rate in real-time on a pulse by pulse basis from the measured frequency of the electrical signal at the output of the feedback control system;
   tracking the pulse rate to detect pulse by pulse variability of the subject's heart rate in real-time; and
   analyzing the tracked heart rate variability in real-time on a beat by beat basis to determine a physiological condition of the subject.

2. The method of claim 1, wherein the feedback control system comprises a phase locked loop (PLL).

3. The method of claim 1, further comprising illuminating the skin of the subject to produce the incident light.

4. The method of claim 1, wherein the incident light is ambient light.

5. The method of claim 1, further comprising at least one of displaying the electrical signal, recording the electrical signal, and converting the electrical signal to an audio signal.

6. The method of claim 1, wherein the signal is captured by sensing the intensity of reflected light off the skin.

7. The method of claim 6, wherein the captured signal is processed.

8. The method of claim 7, wherein the processing comprises filtering the captured signal to at least one of limit the frequency range, adjust the Automatic Gain Control (AGC), and reduce noise.

9. The method of claim 1, wherein the feeding of the captured signal is performed in real-time.

10. The method of claim 1, wherein the feeding of the captured signal is performed off-line.

11. The method of claim 1, wherein the captured signal is sent wirelessly to a location remote from the capturing.

12. The method of claim 1, wherein the captured signal is recorded.

13. The method of claim 1, further comprising monitoring the tracked frequency.

14. The method of claim 1, wherein the feedback control system comprises a Phase Lock Loop (PLL) comprising a two-input Phase Detector (PD), a Loop Filter (LF) and a Voltage Controlled Oscillator (VCO) and feeding the captured electrical signal further comprises feeding the captured electrical signal to a first of the two-inputs to the PD, feeding a PD output to a LF input, feeding a LF output to a VCO input, and feeding a VCO output to a second of the two-inputs to the PD, and further comprising cleaning the electrical signal of noise and providing fast tracking of the varying underlying frequency.

15. The method of claim 2, wherein tracking the pulse rate over time to detect pulse by pulse variability of the subject's heart rate comprises measuring the rate of change in an output of the PLL to deduce heart rate variability.

* * * * *